(12) United States Patent
Bruhn

(10) Patent No.: US 6,363,770 B1
(45) Date of Patent: Apr. 2, 2002

(54) APPARATUS FOR MEASURING THE CONTENTS OF FOREIGN MATTERS IN A FLOWING LIQUID

(75) Inventor: Ulrik Bruhn, Augustenborg (DK)

(73) Assignee: Danfoss A/S, Nordborg (DE)

( * ) Notice: Subject to any disclaimer, the term of this patent is extended or adjusted under 35 U.S.C. 154(b) by 0 days.

(21) Appl. No.: 09/550,809

(22) Filed: Apr. 18, 2000

(30) Foreign Application Priority Data

Apr. 30, 1999 (DE) .......................................... 199 19 641

(51) Int. Cl.[7] .......................... G01N 33/18; G01N 27/08; G01N 27/28; G01N 37/00
(52) U.S. Cl. ...................... 73/19.01; 73/19.1; 73/61.41; 73/61.51; 73/64.56
(58) Field of Search ............................ 73/19.01, 19.1, 73/19.12, 53.01, 61.41, 61.51, 64.47, 64.55, 64.56, 305, 309, 322.5, 863.23

(56) References Cited

U.S. PATENT DOCUMENTS 3,839,902 A * 10/1974 Scott et al. ................. 73/61.51
4,935,726 A * 6/1990 Buro et al. ................. 73/61.51

FOREIGN PATENT DOCUMENTS

GB 2005421 * 4/1979 ................. 73/19.1

* cited by examiner

*Primary Examiner*—Daniel S. Larkin
(74) *Attorney, Agent, or Firm*—Lee, Mann, Smith, McWilliams, Sweeney and Ohlson

(57) ABSTRACT

Apparatus for measuring the contents of foreign matters in a flowing liquid, in particular a buoyant apparatus, which has a housing (1) of which at least one wall section (2) is intended to be brought into contact with the liquid, and has a preferably spherical arched outer side and in a hole (4) a sensor (9) for the foreign matter. The sensor (9) has on its outer side in the area of the hole (4) a diaphragm (10) which is permeable to the foreign matters that are to be measured and which is arched and flush with the outer side of the wall section (2). In order to increase the flow velocity in the area of the diaphragm so that no contaminations remain adhered to the outer side of the diaphragm (10) thus influencing its permeability and thereby the measuring ability of the apparatus, the arched outer side of the wall section (2) is equipped with guiding surfaces (11) for the liquid, which project from it and extend transversely to the hole. These guiding surfaces (11) concentrate the flow in the direction of the diaphragm (10) hereby increasing the flow velocity.

7 Claims, 4 Drawing Sheets

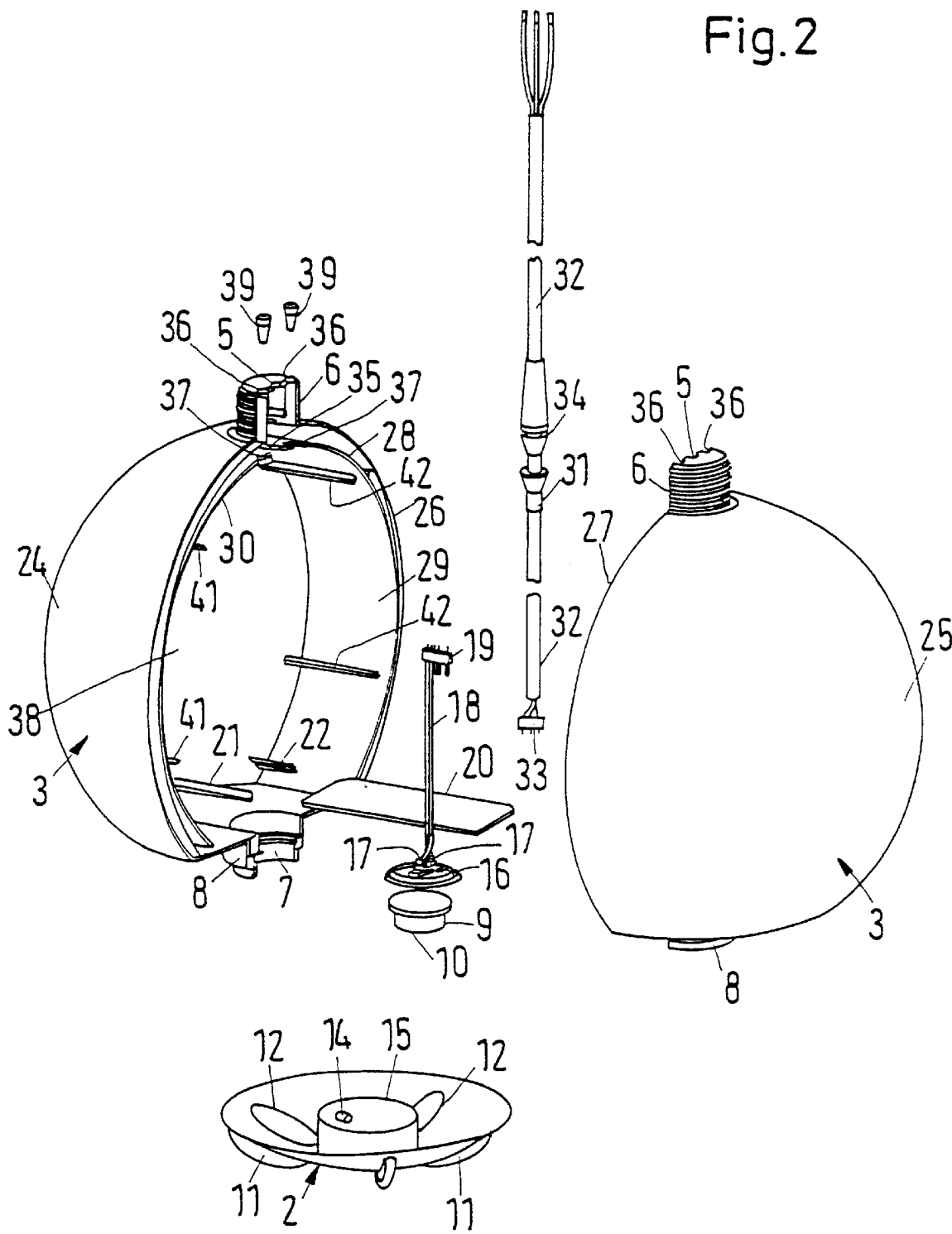

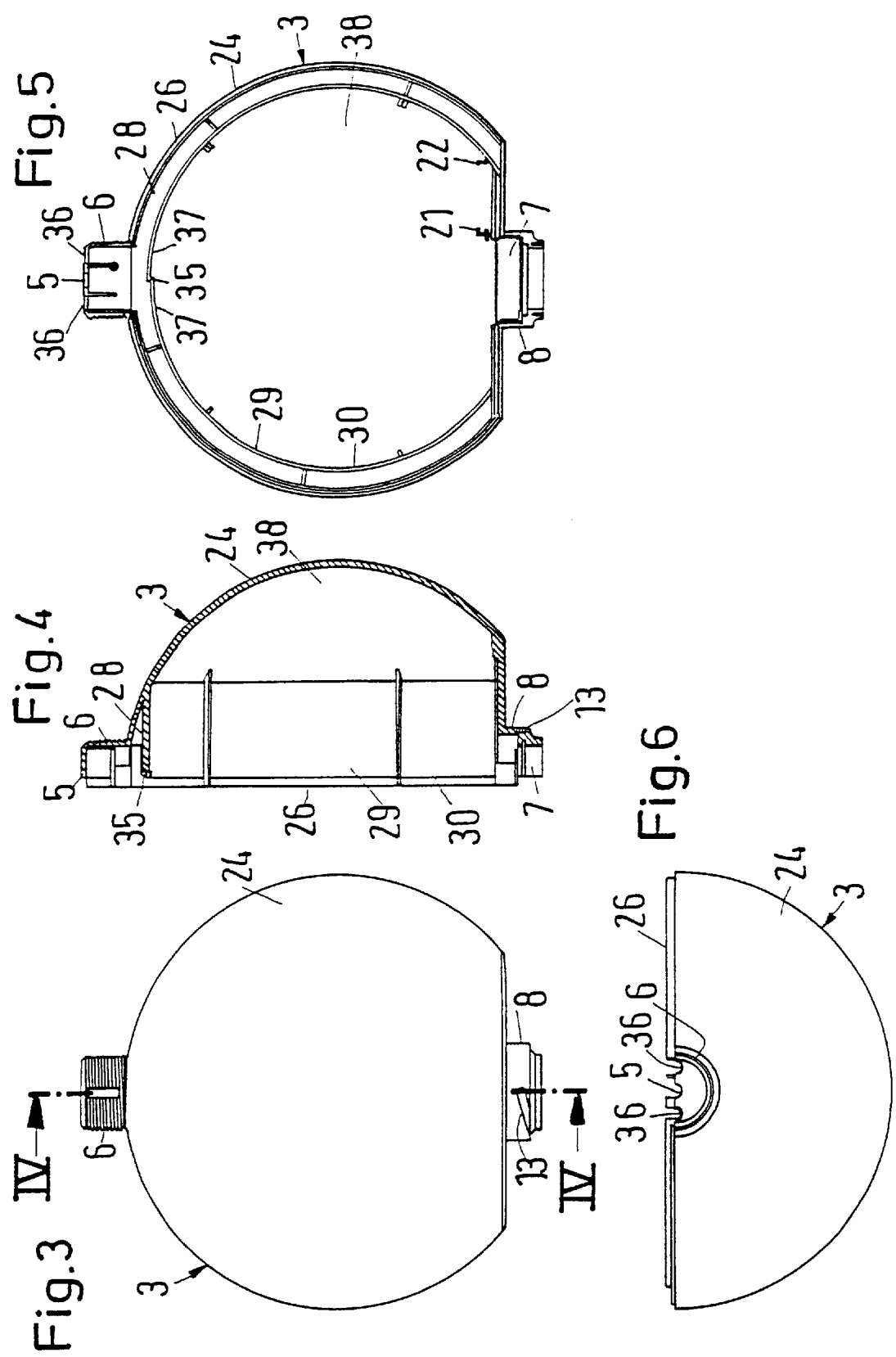

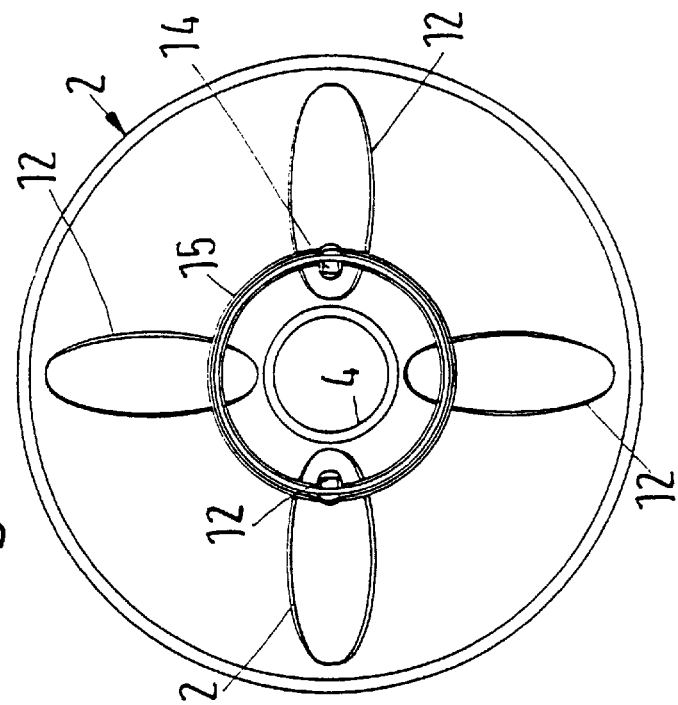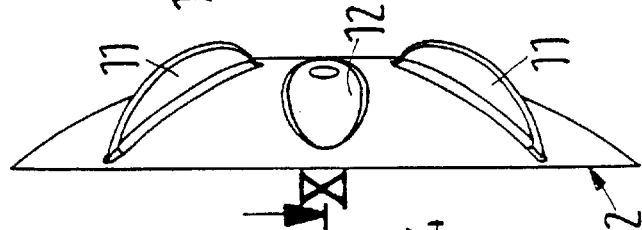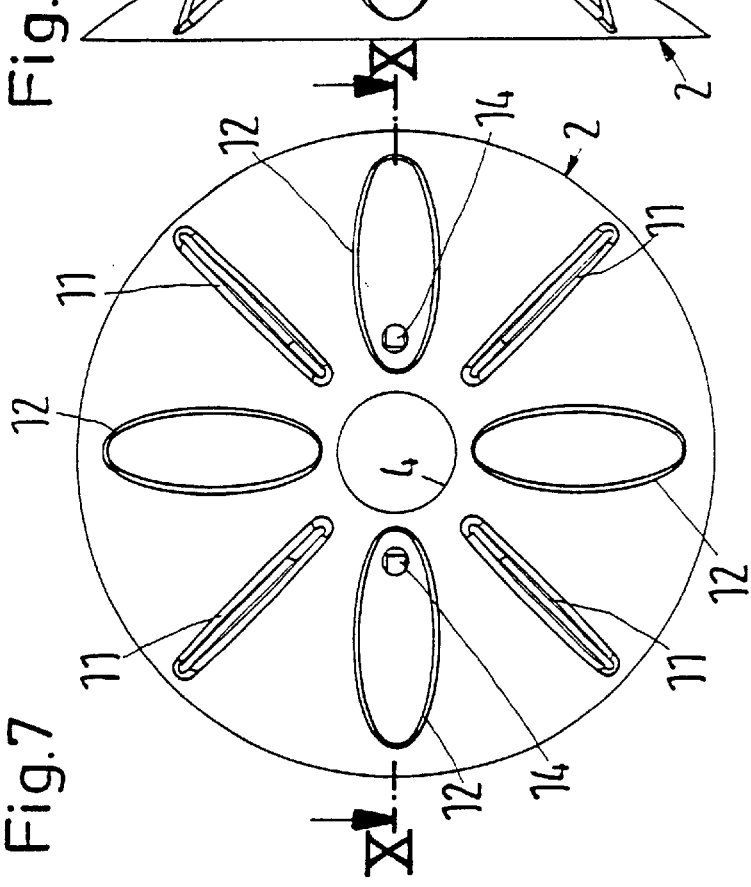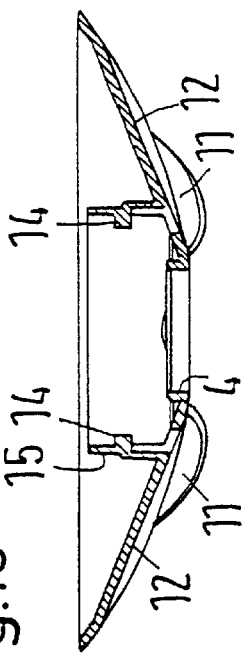

APPARATUS FOR MEASURING THE CONTENTS OF FOREIGN MATTERS IN A FLOWING LIQUID

BACKGROUND OF THE INVENTION

The invention relates to an apparatus for measuring the contents of foreign matters in a flowing liquid, in particular a buoyant apparatus, which has a housing where at least one wall section is to be brought into contact with the liquid, and exhibits a preferably spherical arched outer side and a sensor in a hole for the foreign matter, the outer side of which in the area of the hole is permeable to the foreign matters that are to be measured, and flushes with the arched outer side of the wall section.

An apparatus of this kind is known from GB 2 005 421 A. It serves to analyze wastewater, in particular for the measurement of the oxygen content. Besides, it can be used to measure nutrient solutes in the water, e.g. nitrates and phosphates. The housing has the form of a hollow ball, which is manufactured with two diametrically opposing holes in a rotational injection moulding process. A through-going pipe is adhered to the holes, and a further pipe incorporating the sensor screwed into it is inserted to an extent, that its outer side formed by a front end diaphragm flushes with the outer side of the housing. The diaphragm is also essentially arched in a ball shape. The ball-shaped form of the housing and the arching of the diaphragm gives the advantage, that a flowing liquid, in which the apparatus is partly immersed or is floating, is kept free from contaminations, for example fouling or an oil film, and thus will not impair or destroy the measuring ability of the sensor.

SUMMARY OF THE INVENTION

The object of the invention is to achieve an apparatus of the already described type where the velocity of the liquid is increased further in the area of the outer side of the sensor which is in contact with the liquid.

According to the invention, the object is reached in that the arched outer side of the wall section has guiding surfaces for the liquid extending transversely to the hole.

Due to the the guiding surfaces the liquid flow is concentrated on the arched outer side of the mentioned wall section of the housing and, consequently, on the outer side of the sensor which has the diaphragm, and its flow velocity is increased. In this way, the risk of a contamination of the diaphragm is further reduced.

Preferably, it is arranged, that the guiding surfaces extend radially to the hole. By this design, the liquid flow will be led relatively precise over the centre of the diaphragm.

Further, the guiding surfaces can be arranged around the hole at equal angular distances. In this way, the liquid flow is led over the diaphragm even if it is somewhat tilted in relation to the guiding surfaces.

Principally, the guiding surfaces can be made by the side walls of slots. Preferably they are, however, constructed by means of thin walls which project from the outer side of the wall section. These walls require less material and ensure an essentially laminar flow, as long as they extend in the flow direction.

The free edge of the walls can be arched to the outer side whereby their flow resistance remains low, as long as they extend in the direction of flow.

The outer arched wall section of the housing can be detachably connected with the other part of the housing.

The detachable connection enables a quick assembly and if necessary a quick replacement of the sensor.

The detachable connection could be constructed as a screw connection. It is, however, preferably constructed as a bajonet socket which makes it possible particularly quick to loosen, respectively connect, the arched wall section of the housing with the rest of the housing part.

BRIEF DESCRIPTION OF THE DRAWINGS

In the following the invention will be described with a preferred embodiment together with the drawing. Herein shows.

DESCRIPTION OF THE PREFERRED EMBODIMENT

Figure 1:
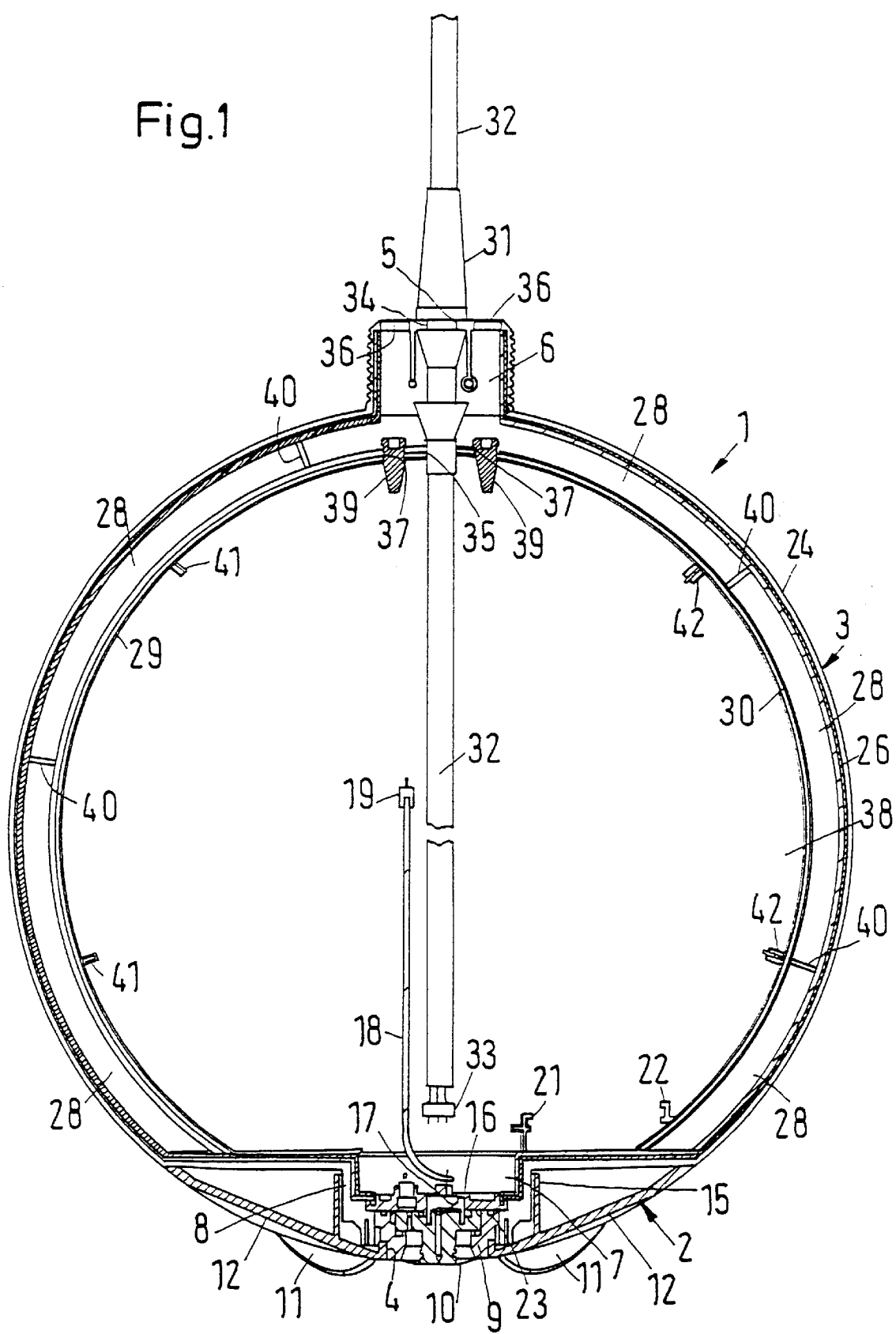
FIG. 1 a cross-section through a metering apparatus according to the invention, FIG. 2 an explosion drawing of the metering apparatus according to FIG. 1, FIG. 3 a side view of a somewhat hemispheric housing part of the metering apparatus according to the invention, FIG. 4 sectional cut away IV—IV of the housing part according to FIG. 3, FIG. 5 an inner view of the housing part according to FIG. 3, FIG. 6 a plan view of the housing part according to FIG. 3, FIG. 7 an outer view of another housing part of the inventive apparatus, FIG. 8 a side view of the housing part according to FIG. 7, FIG. 9 an inner view of the housing part according to FIG. 7 and FIG. 10 sectional cut away X—X of the housing part according to FIG. 7.

According to FIGS. 1 and 2 the inventive apparatus for measuring the contents of foreign matters, such as oxygen, nitrate, or phosphate in a fluid, in particular waste water, contains a spherical arched housing (1) of thermoplastic synthetic material, preferably polybutylenterephtalate. The housing (1) is essentially hollow making the apparatus bouyant. It has a wall section (2) at the bottom, approximately in the form of a section of a hollow ball, and an upper wall section (3). The wall section (2) has a hole (4), and the wall section (3) has an upper through-hole (5) in a connection piece (6) which is provided with an outside threading, and a through-hole (7) at the bottom in a connection piece (8).

In the hole (4) of the wall section (2) a sensor (9) projects, which is arranged in the housing (1) and shown schematically in FIG. 2. This sensor (9) is the actual measuring cell of the apparatus. The sensor (9) has a diaphragm (10) which is permeable to the foreign matters dissolved in the liquid which are to be measured. The diaphragm (10) forms the outer side of the sensor (9) and is arched towards the outside, whereby it is flush with the outer side of the wall section (2).

The arched outer side of the wall section (2) has guiding surfaces (11) for the fluid, projecting radially and extending transversely to the hole (4) (see also FIGS. 7–10). In total, there are four guiding surfaces (11), which are arranged at equal angular distances (see FIG. 7), extending radially to the hole and having thin walls with free borders which are arched towards the outside. If the apparatus is placed in a flowing liquid, the control surfaces (11) cause the flow to concentrate around the hole (4) and consequently to the diaphragm (10) of the sensor (9), and the increased flow velocity in the area of the diaphragm (10) will to a great extent prevent an accumulation of contaminations on the outer side of the diaphragm (10), such as fouling or oil that are contained in the water. Hereby, the permeability of the diaphragm (10) and thus the measuring ability of the apparatus is maintained for a longer time, as would be the case without the guiding surfaces (11). Only four guiding surfaces (11) are shown, however, any number of surfaces can be chosen.

For optical reasons only, oval grooves (12), which could also be omitted, are placed between the guiding surfaces (11) in the outer side of the wall section (2).

The wall section (2) is detachably connected with the wall section (3), which forms the rest of the housing (1), by means of a bayonet socket (13,14), which is formed by the connection piece (8) (see FIGS. 3 and 4) having slots (13) on its outer side of which only one is shown, and radially projecting studs (14) (see FIGS. 7,9, and 10), which are placed on the inner side of a connection piece (15) surrounding the hole (4), which are frictionally engaged in the slots (13). The detachable connection in form of the bayonet socket (13,14) enables a quick replacement of the sensor (9) by unfastening the bayonet socket. For this purpose the built-in sensor (9) is in electrical contact with an essentially plate like connector (16). The connector (16) has contact springs (17), which are connected via a flexible cable (18) and a plug (19) at the free end of the cable to corresponding plug sockets on a printed circuit board (20) shown in a diagram in FIG. 2. To simplify the illustration, the components necessary for the printed circuit board (20) have been left out in the drawing. A sealing ring (23) (FIG. 1) is built in between the sensor (9) and the connector (16).

The wall section (3) consists of two housing parts (24) and (25) which are essentially identical (FIGS. 1 to 6). The housing parts (24,25) are connectable at their edge sections (26,27) and have on their inner side an inner wall consisting of two essentially identical wall parts (29), of which only one is shown in the FIGS. 1,2,4, and 5, which bridges the edge sections (26,27) in the connected state, and delimits an intermediate space (28) together with the outer wall of the housing (1). The wall parts lie opposite the edge section (26) of the housing parts (24,25) and they meet via their edges when the housing parts (24,25) are connected.

Prior to connecting the housing parts (24,25), a leadthrough part (31) for a cable (32), the inner end of which is connected to a plug (33), is inserted into one half of the through-hole (5) of the connection piece (6), whereby the edge of the through-hole (5) engages with a circular groove (34) of the lead-through part (31). At the same time the lead-through part (31) is fastened in a passage (35) which is formed in the edges (30) of the inner wall parts (29). Furthermore, the printed circuit board (20) is pushed into the guides of the rails (21,22) and the connector (16) is placed in the opening (7) of the connection piece (8). The plugs (19) and (33) are mounted into corresponding sockets on the printed circuit board (20), and the housing parts (24,25) are connected. Thereafter, an age-hardable material in the form of an adhesive polyurethane is filled through the upper part of the connection piece (6) and through the free openings (36) and (37) of the inner wall, which is formed by the wall parts (29). The interior (38) of the housing (1) is at least filled until the printed circuit board (20) and its components are encapsulated. The openings (37) are then sealed by means of rubber-elastic stopper plugs (39) as shown in FIG. 1, whereafter the intermediate space (28) is filled through the openings (36) with the same adhesive material which is not yet age-hardened. The outer wall is connected with the inner wall by means of ribs (40), which serve as stiffening pieces, and have passages (not shown) for the adhesive material, in order that the material can fill out the entire interior (28) between the outer and the inner wall of the housing (1). After the age-hardening of the material in the interior (38) and in the intermediate space (28), the two housing parts (24,25), firstly, and, secondly, the wall parts (29) of the inner wall are sealed and the outer and the inner wall combined with each other, and the printed circuit board (20), including the components mounted, is stably encapsulated.

The housing parts (24,25) and the inner wall parts (29) together with the ribs (40) and the stiffening ribs (41) and (42) on the interior of the wall parts (29) as well as the rails (21,22) can all be produced by injection moulding with one moulding tool, and the same moulding tool can be used for the housing parts (24,25) and the inner wall parts (29). Further, after having placed the internal parts and connected the housing parts (24,25), the filling of the adhesive material into the interior (38) and the intermediate space (28) as well as the age-hardening of the material can practically take place in the same manufacturing step. Following this, the sensor (9) mounted in the lower wall section (2) can in a simple manner be connected with the connector (16) by connecting the two wall sections (2) and (3) by means of the bayonet socket (13,14).

The production of the measuring apparatus is thus inexpensive and can be carried out quickly. Besides, after opening of the bayonet socket (13,14), the sensor (9) can if necessary be replaced quickly, which however due to the almost automatic cleaning effect by the increased flow velocity between the guide surfaces (11) would be required at much bigger time intervals than without the guide surfaces (11). At the same time the guide surfaces serve as a handle for manipulating the bayonet socket.

At the connecting piece (6) a stationary fastener can be connected which makes it possible to have only the wall section (2) of the measuring apparatus immersed in the flowing fluid. However, the fastener can be omitted, for instance if the fluid is not flowing. In that case the measuring apparatus can be swimming above the water to an extent, that only the lower wall section (2) will immerse into the fluid, firstly because the centre of gravity of the measuring apparatus is just below the centre of the housing (1) and the filler material can be filled extensively into the interior (38). In that case only the lower wall section (2) would be exposed to the fluid and to contamination if the fluid is contaminated.

What is claimed is:

1. Apparatus for measuring the contents of foreign matter in a flowing liquid, the apparatus having a housing with at least one wall section intended to be brought into contact with the liquid, the wall section having a spherical arched outer side and a hole for a sensor for the sensing of foreign matter, the sensor having an outer side which in the area of the hole is permeable to the foreign matter that is to be measured, the outer side of the sensor being generally flush with the arched outer side of the wall section, and including guiding surfaces for the liquid, extending transversely to the hole, on the arched outer side of the wall section.

2. Apparatus according to claim 1 in which the guiding surfaces extend radially to the hole.

3. Apparatus according to claim 1 in which the guiding surfaces are spaced with equal angular distances around the hole.

4. Apparatus according to claim 1 in which the guiding surfaces comprise thin walls which project from the outer side of the wall section.

5. Apparatus according to claim 4 in which the thin walls have free edges arched towards the outer side of the wall section.

6. Apparatus according to claim 1 in which the arched wall section of the housing is detachably connected to the housing.

7. Apparatus according to claim 6 in which the detachable connection is a bayonet socket.

* * * * *